United States Patent [19]

Brugirard

[11] 4,315,743
[45] Feb. 16, 1982

[54] SYRINGES FOR INJECTING PASTY PRODUCTS

[76] Inventor: Jean-Louis Brugirard, Le Clos - Saint Maurice sur Dargoire, 69440 Mornant, France

[21] Appl. No.: 132,753

[22] Filed: Mar. 24, 1980

[51] Int. Cl.³ .............................................. A61C 5/04
[52] U.S. Cl. ...................................... 433/90; 222/566
[58] Field of Search ................ 433/90, 89, 80, 85; 222/499, 566, 567, 568, 570; 128/239, 247

[56] References Cited

U.S. PATENT DOCUMENTS

| 165,054 | 6/1875 | Baldwin | 222/566 |
|---|---|---|---|
| 416,977 | 12/1889 | Wilder | 128/239 |
| 1,092,701 | 4/1914 | Edwards | 433/90 |
| 2,102,591 | 12/1937 | Hagemeier | 433/90 |
| 2,381,785 | 8/1945 | Thompson | 433/90 |
| 3,374,789 | 3/1968 | Maurer | 128/239 |
| 3,417,971 | 12/1968 | Blank et al. | 433/90 |
| 3,436,828 | 4/1969 | Dragan | 433/90 |
| 3,459,175 | 8/1969 | Miller | 128/239 |
| 3,478,430 | 11/1969 | Park et al. | 433/80 |
| 3,854,209 | 12/1974 | Franklin et al. | 433/90 |
| 3,943,628 | 3/1976 | Kronman et al. | 433/89 |
| 4,043,042 | 8/1977 | Perfect | 433/90 |

FOREIGN PATENT DOCUMENTS

| 679669 | 2/1964 | Canada | 433/90 |
|---|---|---|---|
| 617086 | 8/1935 | Fed. Rep. of Germany | 433/90 |
| 654347 | 5/1938 | Fed. Rep. of Germany | 433/90 |
| 590109 | 6/1925 | France | 128/239 |

Primary Examiner—Gene Mancene
Assistant Examiner—John J. Wilson
Attorney, Agent, or Firm—Dowell & Dowell

[57] ABSTRACT

The present invention relates to improvements in syringes for injecting pasty products, wherein the end of the body thereof comprises a screwed stopper provided with a groove and an oblique channel in the outer opening of which is fixed the endpiece of a needle. To clean the syringe, the stopper is unscrewed and the residue, contained in one piece in the groove and in the channel, is extracted. The present invention is more particularly applicable in dentistry.

6 Claims, 7 Drawing Figures

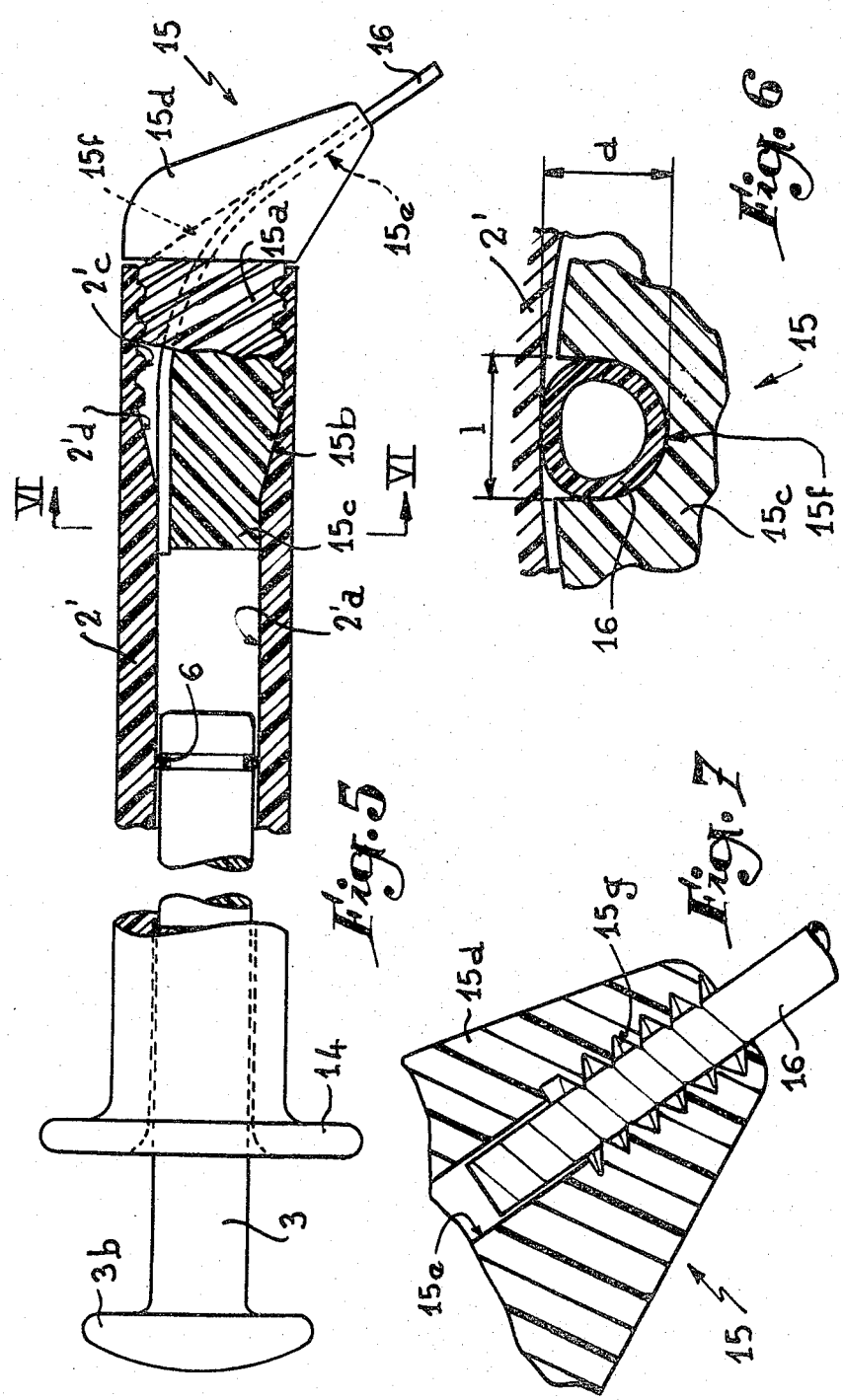

SYRINGES FOR INJECTING PASTY PRODUCTS

The present invention relates to improvements in or relating to syringes intended for injecting pasty products and more particularly products which polymerise in a relatively short time.

Such syringes are used in particular for taking impressions intended for making dentures. A pasty gel is often used which polymerises within 2 to 3 minutes.

Known syringes generally comprise a needle oriented obliquely with respect to the longitudinal axis of their body, said needle being integral with a threaded endpiece which screws in an oblique boss on the syringe. The latter is therefore constituted by a hollow elongated body from which it is difficult to extract the polymerised residues of gel. These residues which are as hard as a hard rubber can only be ejected by pushing them by means of a rod passing through the threaded bore which receives the endpiece of the needle, but this is a random procedure.

On the other hand, the filling of this syringe by a pasty gel is rendered very difficult and long due to the narrowness of the syringe body.

It is an object of the improvements according to the present invention to remedy these drawbacks and to enable a syringe to be produced which responds better than heretofore to the various desiderata of the art.

According to the invention, means are provided allowing the complete removal of the polymerised residue which appears in a syringe for injecting a pasty gel hardening in time.

The invention will be more readily understood on reading the following description with reference to the accompanying drawings, in which:

FIG. 5 illustrates in longitudinal section a further preferred embodiment according to the invention.

FIG. 6 is a section along VI—VI (FIG. 5) on a larger scale.

FIG. 7 is a view similar to that of FIG. 6, but showing a variant.

Figure 1:
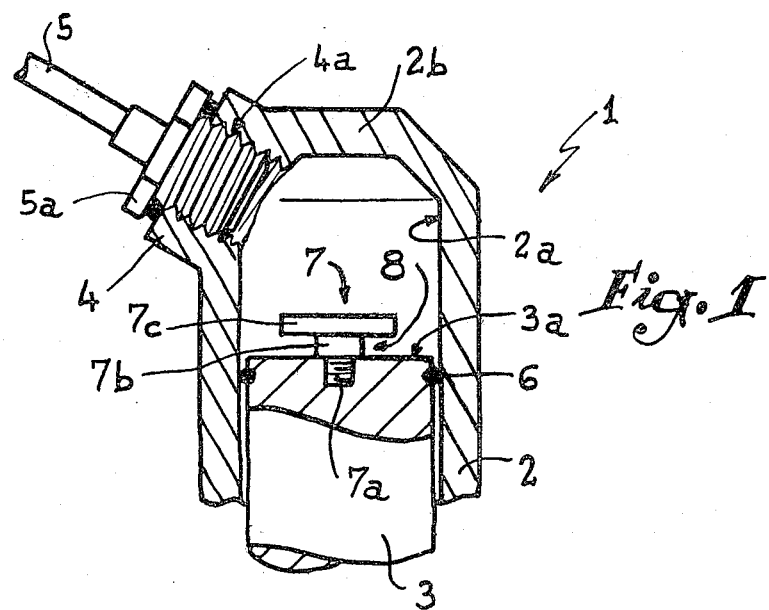
FIGS. 1 and 2 show in longitudinal section a conventional syringe comprising the improvements according to the invention.

Referring now to the drawings, FIG. 1 shows a syringe 1 intended for injecting a pasty gel which polymerises once it has been expelled. Such a syringe essentially comprises a body 2 and a plunger 3 adapted to slide hermetically in the bore 2a of the body 2. This latter comprises a transverse end partition 2b taking the form of a truncated cone whose side face is fast with a boss 4 provided with a central tapped hole 4a whose geometrical axis is oriented obliquely with respect to that of the body 2. The threaded endpiece 5a of an injecting needle 5 is screwed in the hole 4a. Such an arrangement is found in the majority of syringes presently used in dentistry.

An O-ring 6 cooperates with the plunger 3 to ensure the tightness between said plunger and the bore 2a of the body 2.

According to the invention, the inner end of the plunger 3 is provided with an undercut piece made in the form of a stud 7. This stud comprises a lower threaded end 7a which is screwed in a corresponding hole of the plunger, then an intermediate bearing surface 7b which abuts against the end face 3a of the plunger 3, and a head 7c which determines an annular space 8 with the end 3a. When the plunger is at the end of stroke, i.e. when the product contained in the syringe is expelled, the residue polymerises around the stud 7 and in particular in space 8 with the result that, on withdrawing the plunger, this residue is easily extracted.

Figure 2:
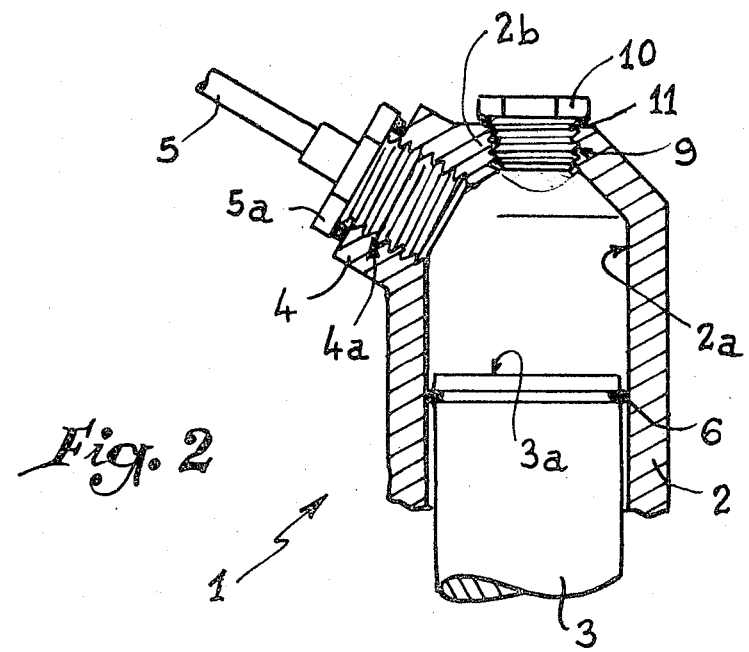

According to the variant of FIG. 2, the partition 2b is provided at its centre with a tapped hole 9 closed by a stopper 10 whose head cooperates with an O-ring 11. The end 3a of the plunger 3 is smooth, with the result that the residue of polymerisable product remains in the bottom of the bore of the body.

To clean said body, it suffices to unscrew the stopper 10 and to act axially on the residue in the direction of the opening of the syringe to drive it out for example by means of a rod whose diameter is similar to that of the hole 9.

Figure 3:
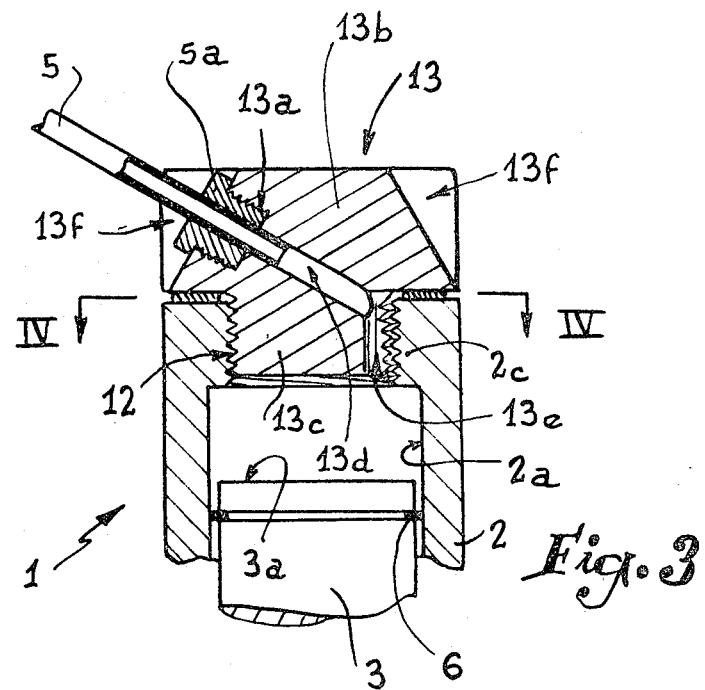
FIG. 3 is a view similar to that of FIGS. 1 and 2, but showing one preferred variant embodiment of the invention.
Figure 4:
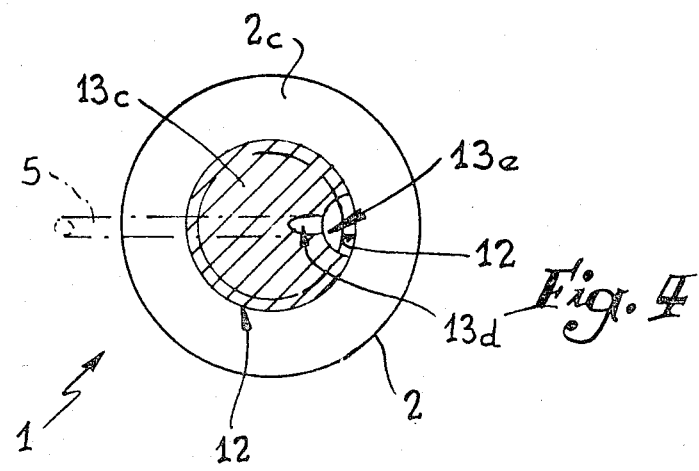
FIG. 4 is a section thereof along IV—IV (FIG. 3).

According to a preferred embodiment shown in FIG. 3, the body 2 of the syringe is closed by a flat end partition 2c through which a tapped hole 12 passes. The endpiece 5a of the injecting needle 5 is screwed in an obliquely oriented tapped hole 13a made in the head 13b of a stopper 13 which comprises an extension 13c of smaller diameter adapted to be screwed in the hole 12. The lower face of the head 13b abuts, at the end of screwing, against the outer face of partition 2c via an O-ring. It is observed that the needle 5 is a continuation of a supply channel 13d which opens in a groove 13e milled vertically in the extension 13c, as shown more particularly in FIG. 4.

Functioning follows from the preceding explanations the pasty gel which is located in front of the plunger 3 passes through the groove 13e and penetrates in channel 13d then in needle 5 so that it is expelled outwardly under pressure by axial displacement of the plunger 3. When the latter is at the end of stroke, there is virtually no residue apart from what is contained in groove 13e and in channel 13d. The polymerised product located in the groove is easily extracted as the groove is open to the outside. As the residue contained in groove 13e and in channel 13d is in one piece, the product located in the channel is extracted with that contained in the groove. The needle is cleaned in conventional manner.

It will be noted that the stopper 13 is provided with peripheral hollows 13f enabling, on the one hand, the endpiece 5a of the needle 5 to be placed in position and, on the other hand, means for tightening and loosening said stopper to be provided.

The needle 5 may, of course, be connected in different manners. For example, the nut or threaded endpiece 5a may be eliminated and replaced by an elastic tubular sleeve, the metal needle 5 extending to the beginning of the channel 13d. Conversely, the needle 5 could be constituted by a tube made of plastics material, for example "nylon", the tubular sleeve being made of steel.

The needle 5 may thus be constituted simply by the tube of plastics material. The inner part of this tube would then extend along the channel 13d and the groove 13e, said tube being immobilised by its curve at the junction of the channel and the groove.

According to a preferred embodiment of the invention, which is illustrated in FIGS. 5 to 7, the body 2' of the syringe is made of moulded material of which one of the ends is provided with a gripping flange 14 intended, as is known, to facilitate the driving-in of the head 3b of the plunger 3. It will be observed that the bore 2'a of the body opens out, opposite the flange 14, in a tapped part 2'c of larger diameter than the one of this bore. This tapped part preferably comprises a screw thread with three threads. It is connected to the bore 2'a by a conical part 2'd.

The end of the body 2' in question is closed by a stopper 15 provided on its periphery with a thread 15a corresponding to the thread 2'c and which extends rearwardly in a truncated endpiece 15b adapted to cooperate hermetically with the part 2'd of the bore. This endpiece continues into a cylindrical lug 15c cooperating without clearance with the bore 2'a. The stopper 15 further comprises an obliquely oriented head 15d which is provided with a longitudinal channel 15e. The latter terminates in a radially oriented groove or notch 15f which opens out on the side faces of the thread 15a of the end-piece 15b, as illustrated in FIG. 6. A tube 16 made of plastics material, advantageously polytetrafluorethylene is engaged in the channel 15e and in the notch 15f. It will be noted that the diameter of the tube 16 is greater than the depth of the notch 15f the width 1 of which being equal to said diameter. The tube may therefore be easily engaged in the notch 15f. The tube is made fast with the stopper by abutment against the bore 2'c, its inner end slightly extending beyond the stopper. In fact the distance d between the bottom of the notch and the side of the bore 2'c, at the level of the cylindrical lug 1c, is less than the diameter of the tube 16. As non restrictive example the diameter of the tube is 1,15 millimeters, the width of the notch is also 1,15 millimeters and the distance d is 1,10 millimeters. It will be understood that the tube is wedged by radial pressure and that a tight seal is obtained between this tube and the bore 2a of the body due to the above dimentional characteristics.

With a view to avoiding the drops in pressure in the tube as much as possible, the bottom of the notch, on which the tube rests, is made in the form of a curved passage where it approaches the channel 15e. In a preferred embodiment, the radius of this curve is equal to five times the inner diameter of the tube.

Due to this arrangement, the needle may easily be changed, involving only a very slight loss each time the matter polymerises inside.

In another embodiment shown in FIG. 7, the channel 15e is provided to terminate in a tapped part 15g of which the diameter is smaller than that of the tube 16. A short section of this tube may thus be engaged by screwing, which section is connected to the head 15d of the stopper 15 by wedging with respect to the above-mentioned tapping.

When the matter to be expelled has solidified in the groove and the section of tube acting as needle, the latter tube may easily be dismantled by unscrewing it, the residue of matter located in the groove opens on the lateral face of the stopper.

A syringe is thus produced for injecting polymerisable pasty gel, which is particularly easy to clean.

If part of the residue remains between the end of the plunger 3 and the end partition 2c of the body 2, it may easily be ejected by acting thereon through the hole 12, as explained with reference to FIG. 3.

The preceding description has, of course, only been given by way of non-limiting example and the replacement of details of execution described by any other equivalents would not depart from the scope of the invention.

What is claimed is:

1. A dental syringe for ejecting a pasty material, comprising:
   (a) a hollow body having an axial bore therethrough the bore being open at one end and being internally threaded at its other end;
   (b) a plunger extending into the body through its open end and slideable in the bore;
   (c) a stopper having a threaded part cooperatively receivable in the threaded end of the bore, the stopper having a head extending therefrom and the head having a channel extending through it at an oblique angle to the axis of the bore and the channel communicating with the bore in the body;
   (d) a flexible tube removably inserted in the channel and sealed thereto, the tube having a portion extending from the channel beyond the head; and
   (e) said stopper further comprising a longitudinal notch extending along the side of the threaded part of the stopper parallel to the axis of the bore and extending into said oblique channel and shaped to receive said flexible tube, the notch distorting the tube against the bore and wedging it in place when the stopper is screwed into the bore.

2. The dental syringe as claimed in claim 1, wherein the head has a curved passage connecting the oblique channel with the axial notch and shaped to receive and bend the tube.

3. The dental syringe as claimed in claim 2, wherein said threaded part of the stopper includes a truncated conical part extending toward the bore therefrom and supporting a cylindrical part, the notch extending along the sides of said parts, and the bore of the body having conical and cylindrical portions cooperatively receiving said parts and sealing thereagainst.

4. The dental syringe as claimed in claim 3, wherein the outside diameter of the tube is equal to the width of the notch, and wherein in the cylindrical part the depth of the notch is less than said diameter to compress and seal the tube between the notch and the body bore.

5. The dental syringe as claimed in claim 4, wherein the curved passage in the head has a radius of curvature substantially equal to five times the inner diameter of the tube.

6. The dental syringe as claimed in claim 5 wherein the channel in the head has a threaded end and wherein the inside diameter of the threads is less than the outside diameter of the tube which is supported by the threads when screwed thereinto.

* * * * *